United States Patent
Reiner et al.

(12)

(10) Patent No.: US 6,439,721 B1
(45) Date of Patent: Aug. 27, 2002

(54) DEVICE FOR VIEWING THE FUNDUS OF THE EYE

(75) Inventors: Josef Reiner, Köln; Rainer Kirchhuebel, Asslar, both of (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 09/429,131

(22) Filed: Oct. 28, 1999

(30) Foreign Application Priority Data

Oct. 29, 1998 (DE) ..................................... 298 19 341 U
Apr. 8, 1999 (DE) ..................................... 299 05 970 U

(51) Int. Cl.[7] ................................................ A61B 3/00
(52) U.S. Cl. ...................................................... 351/219
(58) Field of Search ................................. 351/205, 219, 351/246, 247, 216, 221, 160 R

(56) References Cited

U.S. PATENT DOCUMENTS 5,784,147 A * 7/1998 Volk ........................... 351/219

FOREIGN PATENT DOCUMENTS

DE 38 26 069 2/1990
DE 298 19 341.8 10/1998

* cited by examiner

*Primary Examiner*—George Manuel
(74) *Attorney, Agent, or Firm*—Flynn, Thiel, Boutell & Tanis, P.C.

(57) ABSTRACT

A device for viewing the fundus of the eye, in particular by means of an optical system, has a handle and a lens system fastened to the handle. The lens system has thereby a first lens with a concave lens surface, which can be placed onto the corona of an eye and can be combined with further lenses. Such a device is further developed in such a manner that on the one hand the fundus of the eye can be viewed and on the other hand a quick change for viewing of the foreground of the eye is possible when the device is removed from the beam path between the eye and the optical system. The device is therefore further developed in such a manner that the handle has a mounting for a supplementary lens, which is mounted in viewing direction in front of the lens system, whereby the strength of the supplementary lens is chosen in such a manner that when viewing the fundus of the eye with the device the optical system is actually clearly focused onto the foreground of the eye.

8 Claims, 4 Drawing Sheets

DEVICE FOR VIEWING THE FUNDUS OF THE EYE

FIELD OF THE INVENTION

The present invention relates to a device for viewing the fundus of the eye, in particular by an optical system, for example a microscope, a slit lamp or an indirect ophthalmoscope, wherein the device is equipped with a handle and a lens system fastened to the handle, the lens system has a first lens with a concave lens surface, which can be placed onto the corona of an eye and can be combined with further lenses.

BACKGROUND OF THE INVENTION

Such a device is known, for example, from German Gebrauchsmuster 298 19 341.8. The device is placed onto the eye for viewing the fundus of the eye. It is then possible to view the fundus of the eye with an optical system, for example, a microscope, a slip lamp or an indirect ophthalmoscope. An image of the retina or of the inside of the eye is created at a distance in front of the eye through the action of the first lens, to which image the microscope or another optical system is adjusted.

However, it is necessary during an eye examination or during eye surgery for the physician to alternately view the fundus of the eye and the foreground of the eye. To change the view, the device is either placed onto the eye or is removed from the beam path between the eye and microscope. However, since the microscope is either adjusted to the image of the fundus of the eye, which is created in front of the device, or is adjusted to the foreground of the eye, it is necessary when changing from the one view to the other view of the eye to refocus the microscope or the other optical system. This means in each case a loss of time of a few seconds, which unnecessarily extends the examinations or surgeries. Physicians therefore desire devices with which a change between viewing the fundus of the eye and the foreground of the eye can take place quickly and easily.

SUMMARY OF THE INVENTION

The basic purpose of the invention it therefore to provide a device with which the fundus of the eye can be viewed and which quickly changes for viewing of the foreground of the eye when the device is removed from the beam path between the eye and optical system.

This purpose is attained according to the invention in such a manner that a handle is provided with a mounting for a supplementary lens, which is moved in a viewing direction in front of the lens system, whereby the strength of the supplementary lens is chosen in such a manner that when viewing the fundus of the eye with the device, the optical system is clearly focused onto the foreground of the eye.

The supplementary lens inserted between the lens system and the optical system shifts the image of the fundus of the eye, namely of the retina or the inside of the eye, into a plane, which lies in the area of the foreground of the eye. Thus the microscope or the optical system must be sharply focused onto this plane in order to view the fundus of the eye. When the device with the lens system and the supplementary lens is now removed from the beam path between the eye and the optical system, then the optical system remains focused on the plane in the area of the foreground of the eye so that this area can be viewed directly by the optical system. Thus complicated refocussing of the optical system is removed.

The supplementary lens according to the invention can be a collective lens or collecting lens system, which can be exchangeably held in a mounting. The distance between the supplementary lens and the lens system can be changed according to the present invention.

The device has, in a specific design of the invention, an illuminating device, the outlet surface of which lies within the first lens of the lens system or ends flush with a lens surface of the first lens.

The lens system is advantageously enclosed in a housing, whereby according to the invention the entire device can be sterilized and/or autoclaved.

BRIEF DESCRIPTION OF THE DRAWINGS

Two exemplary embodiments and the operating principle will be discussed in greater detail in connection with the drawings, in which.

DETAILED DESCRIPTION

Figure 1:
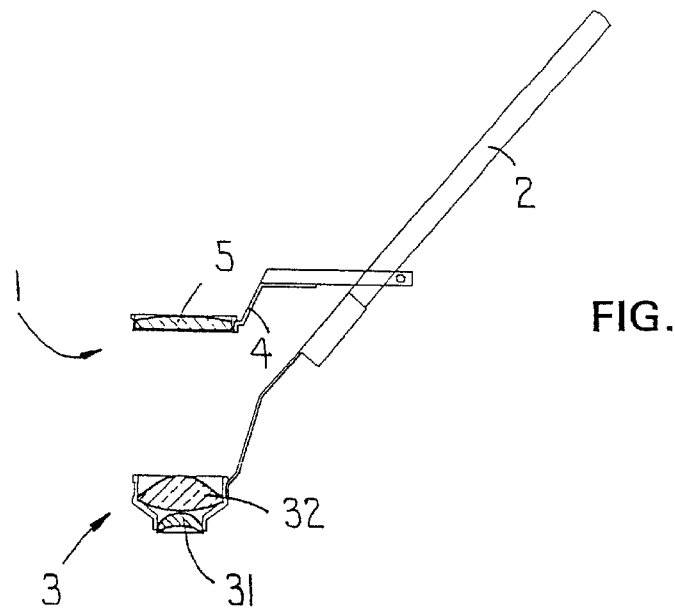
FIG. 1 is a first embodiment of the device of the invention.
Figure 2:
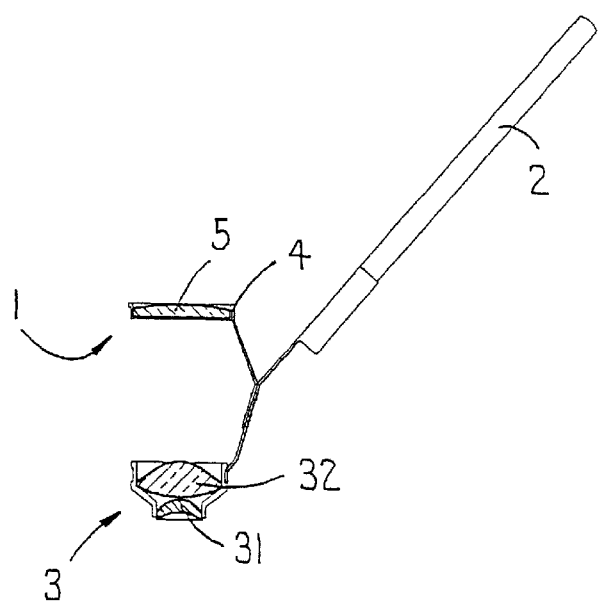
FIG. 2 is a second embodiment of the device of the invention.
Figure 3:
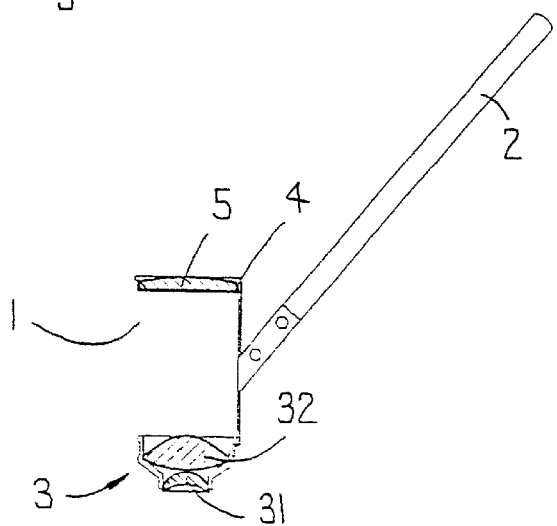
FIG. 3 is a third embodiment of the device of the invention.

Separate embodiments of the device 1 of the present invention are illustrated in FIGS. 1, 2 and 3 and each have a handle 2, to one end of which is fastened an enclosed lens system 3 and to the other end of which is fastened a supplemental lens 5 through a holder 4. The holder 4 can be pivotally connected to the handle 2 so that the distance "e" between lens 5 and the lens system 3 can be adjusted. The illustrated enclosed lens system 3 consists of a first lens 31, which can be placed onto an eye 7 with its concave side, and a second lens 32 arranged in front (on a side of the first lens 31 opposite the subject eye) thereof. The lens system 3 is enclosed in a material which can be sterilized, for example by autoclaving or chemical bath without degrading its performance as a lens system. The enclosed lens system 3 can be constructed of metal, glass and/or plastics which are not deformed under high temperature and pressure experienced in an autoclave.

Figure 4:
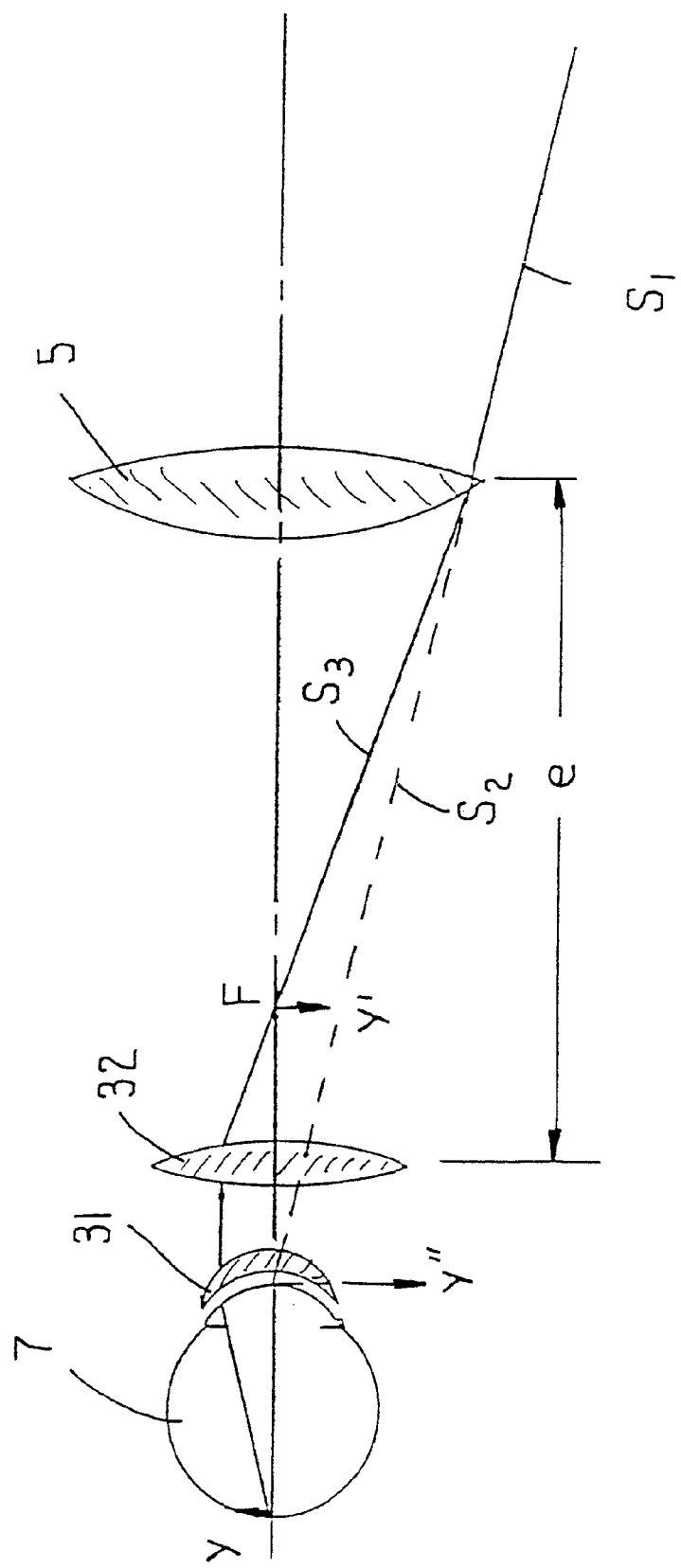
FIG. 4 illustrates the operating principle of the invention.

The operation of the two devices according to FIGS. 1, 2 and 3 will now be discussed in greater detail in connection with FIG. 4. Schematically illustrated is an eye 7 on which the first lens 31 lies with its concave lens surface. The second lens 32 of the lens system 3 is provided in front thereof. The supplemental lens 5 is provided between the optical system (not illustrated in FIG. 4) and the lens system 3, 31, 32, i.e. the optical system would be positioned in front of the supplemental lens 5. An article y positioned on the retina of the eye is illustrated as an intermediate image y' by the lens system 3, 31, 32 in front of the lens system at its focal point F. The optical system is adjusted in such a manner that the cornea of the eye can be clearly viewed without the lens system and the supplemental lens. This is indicated by the uninterrupted beam comprised of actual beam segment $S_1$ and virtual beam segment $S_2$. When the lens system is now moved alone (without supplemental lens) into the beam path between the eye and optical system, a viewer cannot clearly recognize the fundus of the eye since the intermediate image y' is created at the point F in front of the second lens 32, whereas the optical system is sharply focused onto the cornea of the eye. The supplemental lens 5, which is in the beam path between the second lens 32 and the optical system, deflects actual beam segment $S_3$ extending from the lens system 3 to the optical system in such a manner that it arrives as the beam $S_1$, which is now focused at the point F in front of the second lens 32. Thus the focal distance of the optical system is adapted by this supplemental lens 5 in such a manner that the intermediate image y' created at the point F can be clearly viewed. The intermediate image y' at the point F is created for the viewer as a virtual image y" in a plane in the area of the cornea of the eye 7. This is indicated by the virtual beam segment $S_2$. The focal point of the supplemental lens 5 is between the plane of the cornea and the point F to create the virtual image y".

The optical system is advantageously focused in such a manner that the cornea of the eye can be clearly viewed. When the device comprised of the lens system 3, 31, 32 and supplemental lens 5 is moved into the beam path between the eye 7 and the optical system, then the fundus of the eye or the retina of the eye can be viewed immediately without requiring a refocussing of the optical system.

Figure 5:
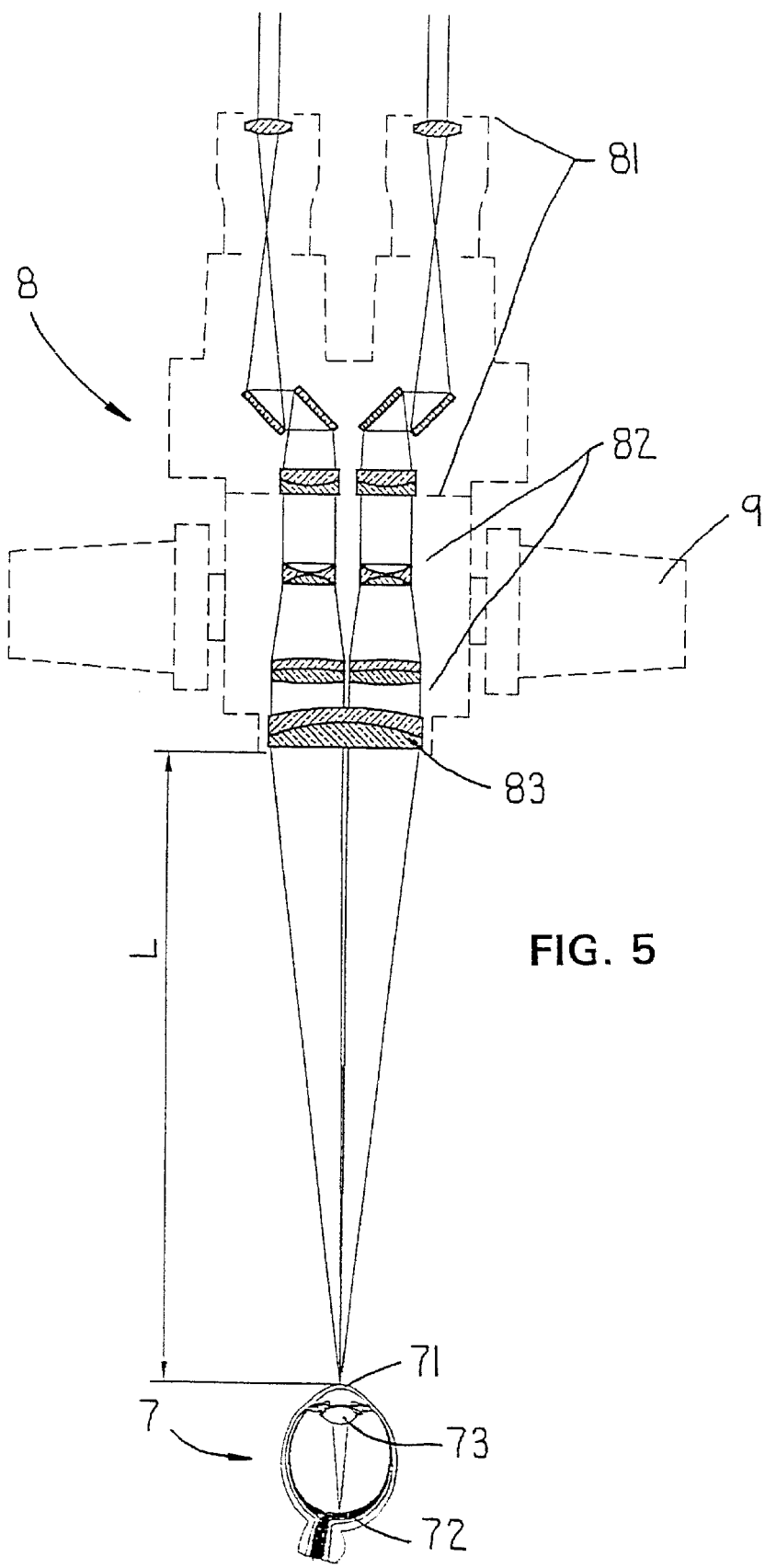
FIG. 5 shows a schematic illustration of a microscope for viewing an eye.

The microscope 8 illustrated in FIG. 5 has an oculary arrangement 81 through which a physician can view the subject eye. The beam path extends from the ocular arrangement 81 through an optical enlargement changer 82 followed by a lens arrangement 83. The microscope 8 is, as is common, enclosed by a schematically indicated housing 9. Such a microscope is known from the state of the art, in particular from the DE 38 26 069.7 so that the further description herein relates essentially to the inventive arrangement of the device 1 and not to the microscope. The microscope 8 is one example of the optical system.

Figure 6:
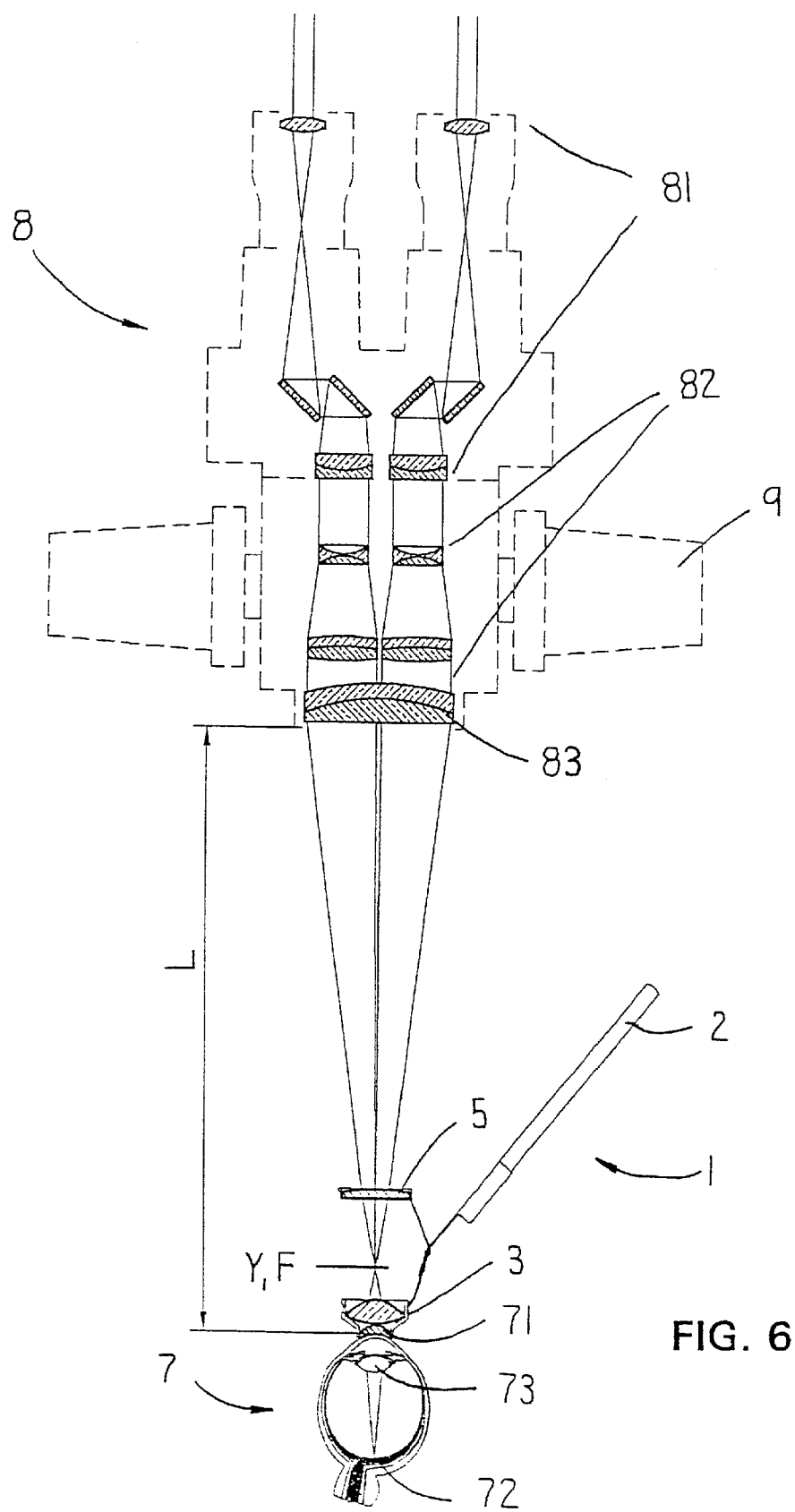
FIG. 6 shows a schematic illustration of the microscope according to FIG. 5 including a device of the invention.

The lens arrangement 83 of the microscope 8 is adjusted in such a manner that the cornea 71 lies in the focus of the lens 83 (FIG. 5). The device 1 of the invention is placed onto the cornea 71 of the eye 7 in the arrangement according to FIG. 6. This device enables the viewing of the retina 72 of the eye 7. An intermediate image y' of the retina at the point F in front of the lens system 3 is thereby created first. The supplemental lens 5 influences the beams extending toward the microscope in such a manner that the intermediate image y' of the lens system 3 is created as a virtual image y" at the plane of the cornea.

The device of the invention makes it possible to change in a simple and quick manner between viewing the cornea 71 and the retina 72 of the eye 7 without requiring refocussing of the optical system, e.g. microscope 8. At the same time it is possible to change the image area with the enlargement changer of the microscope 8 without requiring refocussing of the microscope 8.

Although a particular preferred embodiments of the invention have been disclosed in detail for illustrative purposes, it will be recognized that variations or modifications of the disclosed apparatus, including the rearrangement of parts, lie within the scope of the present invention.

We claim:

1. A device for converting a viewing the fundus of the eye using an optical system to one viewing a surface of the cornea of the eye using the optical system, comprising a handle and a lens system fastened to said handle, the lens system having a first lens with a concave lens surface configured to be placed onto a cornea of an eye and is combined with at least one further lens, the handle having a mounting for a supplementary lens, the first lens establishing a location of a focal point for the surface of the cornea intermediate the first lens and the supplemental lens, and the supplementary lens being mounted in a viewing direction in front of the first lens and having a focal strength focused to the focal point for the surface of the cornea so that when the optical system is set to view the fundus of the eye and the lens system is thereafter oriented intermediate the optical system and the eye with the first lens being placed onto the cornea, the optical system is focused on the surface of the cornea of the eye.

2. The device according to claim 1, wherein the supplementary lens is a collective lens.

3. The device according to claim 1, wherein the supplementary lens is held exchangeably in the mounting.

4. The device according to claim 1, wherein the distance between the supplementary lens and the lens system can be changed.

5. The device according to claim 1, wherein the device has an illuminating device, the light-exiting surface of which lies within a first lens of the lens system or terminates flush with a lens surface of the first lens.

6. The device according to claim 1, wherein he lens system is encased in a housing.

7. The device according to claim 1, wherein the device can be sterilized and/or autoclaved.

8. The device according to claim 1, wherein the lens system is additionally configured so that the placement of the lens system as aforesaid intermediate the optical system and the eye will enable the surface of the cornea to be viewed by the optical system without altering the focus thereof.

* * * * *